United States Patent [19]
Zheng et al.

[11] Patent Number: 5,438,041
[45] Date of Patent: * Aug. 1, 1995

[54] OXYGEN CARRYING MULTIPLE EMULSIONS

[75] Inventors: Shuming Zheng, Chicago; Richard L. Beissinger, Oak Park; Darsh T. Wasan, Darien; Lakshman R. Sehgal, Glenview; Arthur L. Rosen, Wilmette, all of Ill.

[73] Assignees: Illinois Institute of Technology, Chicago; Northfield Laboratories, Inc., Evanston, both of Ill.

[ * ] Notice: The portion of the term of this patent subsequent to Oct. 29, 2008 has been disclaimed.

[21] Appl. No.: 25,608

[22] Filed: Mar. 3, 1993

Related U.S. Application Data

[63] Continuation of Ser. No. 776,062, Oct. 11, 1991, Pat. No. 5,217,648, which is a continuation-in-part of Ser. No. 234,386, Aug. 19, 1988, Pat. No. 5,061,688.

[51] Int. Cl.$^6$ .................. A61K 9/113; A61K 37/14; B01J 13/00
[52] U.S. Cl. ......................... 514/6; 252/309; 252/312; 252/314; 514/832; 514/833; 514/938; 514/939; 514/941
[58] Field of Search ............. 252/309, 312, 314; 514/6, 832, 833, 938, 939, 941

[56] References Cited

U.S. PATENT DOCUMENTS

| | | | |
|---|---|---|---|
| 3,823,091 | 7/1974 | Samejima et al. | 252/312 |
| 3,993,581 | 11/1976 | Yokoyama et al. | 252/312 |
| 4,146,499 | 3/1979 | Rosano | 252/312 X |
| 4,461,717 | 7/1984 | Moore | 252/312 |
| 4,533,254 | 8/1985 | Cook et al. | 366/176 |
| 4,569,784 | 2/1986 | Moore | 252/312 X |
| 4,590,086 | 5/1986 | Takahashi et al. | 252/312 X |
| 4,612,370 | 9/1986 | Hunt | 536/5 |
| 4,714,566 | 12/1987 | Takahashi et al. | 252/314 |
| 4,776,991 | 10/1988 | Farmer et al. | 264/4.3 |
| 4,804,495 | 2/1989 | Bouchez et al. | 252/312 |
| 4,808,334 | 2/1989 | Ezaki et al. | 252/314 |
| 4,866,096 | 9/1989 | Schweighardt | 514/832 X |
| 5,061,688 | 10/1991 | Beissinger et al. | 514/6 |
| 5,217,648 | 6/1993 | Beissinger et al. | 252/314 |

FOREIGN PATENT DOCUMENTS

| | | |
|---|---|---|
| 0038172 | 10/1981 | European Pat. Off. . |
| 0038173 | 10/1981 | European Pat. Off. . |
| 0091183 | 10/1983 | European Pat. Off. . |

OTHER PUBLICATIONS

Szoka, Jr. et al.: "Procedure for Preparation of Liposomes with Large Internal Aqueous Space and High Capture by Reverse Phase Evaporation", *Proc. Natl. Acad. Sci. U.S.A.*, vol. 75, No. 9, pp. 4194–4198, Sep. 1978 Biochemistry.

*Hackh's Chemical Dictionary,* Fourth Edition, Revised and Edited by Julius Grant, McGraw-Hill Book Co., New York 1969, pp. 240, 168 and 169.

International Journal of Pharmaceutics, vol. 11, 1982, pp. 277–308, "The Formulation and Stability of Multiple Emulsions".

T. Davis, W. Asher and H. Wallace, *Artificial Red Cells with Crosslinked Hemoglobin Membranes,* Applied Biochemistry and Biotechnology, vol. 10, 1984.

S. Matsumoto, Y. Kita and D. Yonezawa, *An Attempt at Preparing Water-in-Oil-in-Water Multiple-Phase Emulsions,* Journal of Colloid and Interface Science, vol. 57, No. 2, Nov. 1976.

(List continued on next page.)

*Primary Examiner*—Richard D. Lovering
*Attorney, Agent, or Firm*—Speckman, Pauley & Fejer

[57] ABSTRACT

A process is provided wherein hemoglobin, a fragile material, is formulated into high hemoglobin content water-in-oil-in-water multiple emulsion while maintaining high yields and high oxygen exchange activity. A multiple emulsion of aqueous oxygen carrying material in oil in outer aqueous phase is suitable for provision of oxygen for oxygen transfer processes. A hemoglobin multiple emulsion in physiologically compatible oil in an outer aqueous saline solution is provided in sufficiently small droplet size to provide oxygen flow through blood vessels to desired body tissues or organs thereby providing a blood substitute.

19 Claims, 2 Drawing Sheets

OTHER PUBLICATIONS

S. Matsumoto, Y. Ueda, Y. Kita and D. Yonezawa, *Preparation of Water-in-Olive Oil-in-Water Multiple-Phase Emulsions in an Eatable Form*, Agric. Biol. Chem., 42 (4), 739–743, 1978.

P. E. Keipert and T. M. S. Chang, *In Vivo Assessment of Pyridoxylated Crosslinked Polyhemoglobin as an Artificial Red Cell Substitute in Rats*. vol. 29, pp. 329–333, Trans. Am. Soc. Artif. Intern. Organs, 1985.

P. E. Keipert and T. M. S. Chang, *Pyridoxylated Polyhemoglobin as a Red Cell Substitute for Resuscitation of Lethal Hemorrhagic Shock in Conscious Rats*, vol. 13(1 & 2), pp. 1–15, Biomat. Med. Dev. Art. Org., 1985.

C. M. Borwanker, S. B. Pfeiffer, S. Zheng, R. L. Beissinger, and D. T. Wasan, *Formulation and Characterization of a Multiple Emulsion for Use as a Red Blood Cell Substitute*, Biotechnology Progress, vol. 4, No. 4, 210–217, Dec., 1988.

S. Zheng, R. L. Beissinger, and D. T. Wasan, *The Stabilization of Hemoglobin Multiple Emulsion for Use as a Red Blood Cell Substitute*, Journal of Colloid and Interface Science, vol. 144, No. 1, 72–85, Jun. 1991.

Sehgal, L. R., Gould, S. A., Rosen, A. L., Moss, G. S.: *Appraisal of Red Cell Substitutes: Hemoglobin Solution and Perfluorochemical Emulsions*, Laboratory Medicine, 14:545, 1983.

Gould, S. A., Rosen, A. L., Sehgal, L. R., Moss, G. S.: *Red Cell Substitutes: Hemoglobin Solution or Fluorcarbon?*, J. Trauma, 22:736, 1982.

Gould, S. A., Rosen, A. L., Sehgal, L. R., Moss, G. S.: *Hemoglobin Solutions as Red Cell Substitutes*, Trans. Am. Soc. Art. Int. Organs, 26:350, 1980.

Sehgal, L. R., Rosen, A. L., Gould, S. A., Moss, G. S.: *Polymerized Pyridoxylated Hemoglobin: A Red Cell Substitute with Normal Oxygen Capacity*, Surgery, 95:433, 1984.

Miller, I., *Synthetic Blood Substitutes: Where Are We and Where do We Go From Here?*, CRC, Crit. Rev. BioEng., 149–178, Dec. 1978.

OXYGEN CARRYING MULTIPLE EMULSIONS

CROSS REFERENCE TO RELATED APPLICATIONS

This application is a continuation of application Ser. No. 07/776,062 filed Oct. 11, 1991, now U.S. Pat. No. 5,217,648, which is a continuation-in-part of application Ser. No. 07/234,386 filed Aug. 19, 1988, now U.S. Pat. No. 5,061,688.

BACKGROUND OF THE INVENTION

1. Field of the Invention

A process is provided wherein hemoglobin, a fragile material, is formulated into high hemoglobin content aqueous hemoglobin solution in oil in water multiple emulsions while maintaining high oxygen exchange activity necessary for the below uses. Hemoglobin multiple emulsion having specified properties is suitable for provision of oxygen as a blood substitute and other oxygen transfer processes. A double emulsion of aqueous high hemoglobin content in physiologically compatible mineral oil or fixed oil in an outer aqueous saline solution is provided in sufficiently small droplet size to provide oxygen flow through blood vessels to desired body tissues or organs.

2. Description of Relevant Art

It is important in many physiological and industrial applications to have available an oxygen carrying chemical for provision of oxygen to an oxygen depleted environment. One of the most important applications is provision of an effective oxygen carrying blood substitute. In addition to emergency situations where there are not adequate supplies of whole blood, there are advantages in use of a synthetic blood substitute over the use of whole blood. For example, the efficiency of oxygenation by deficient blood flow in a tissue or an organ resulting from restriction of a blood vessel cannot be treated by use of whole blood, whereas blood substitutes of low bulk viscosity may deliver oxygen through constricted vessels, thereby preventing heart attacks and strokes caused by constriction of the arteries. Use of synthetic blood substitutes also eliminates transmission of blood borne infectious diseases, such as hepatitis and acquired immune deficiency syndrome. Other problems of intolerance or allergy to blood may be solved by synthetic blood substitutes.

An ideal synthetic blood substitute should have high oxygen carrying capacity and low oxygen affinity to permit loading of oxygen in the lungs and releasing of oxygen in the tissue; colloid osmotic pressure close to that of blood plasma; viscosity the same or less than that of whole blood; non-toxicity to the human body; histocompatibility, no antigenic affects; an adequate lifetime in the circulatory system to meet the desired needs for oxygen provision; relatively rapid metabolism or excretion of chemical agents; and adequate storage stability. To date, no blood substitutes have been fully approved for use in the United States of America.

One approach to provision of blood substitutes has been use of media with high passive oxygen solubility, primarily perfluorocarbon emulsions, which have been found to be unstable, have inadequate oxygen carrying capacity, and are toxic to the human. Problems with many perfluorocarbon emulsions have been high oxygen concentrations necessary due to the fluorocarbon emulsion carrying oxygen by passive solubility and the necessity to store the emulsion in the frozen state to retain stability.

The most promising present approaches involve use of chemical hemoglobin in various forms. Although stroma-free hemoglobin solutions have an adequate oxygen carrying capacity, they have high oxygen affinity, high colloid osmotic pressure, possible toxicity, and clearance from the cardiovascular circulation which is too rapid. One problem with stroma-free hemoglobin solutions has been that their oxygen affinity is much higher than that of normal hemoglobin in red blood cells and therefore oxygen is preferentially extracted from the cellular hemoglobin. Sehgal, L. R., Gould, S. A., Rosen, A. L., Moss, G. S.: Appraisal of Red Cell Substitutes: Hemoglobin Solution and Perfluorochemical Emulsions, *Laboratory Medicine*, 14:545, 1983; Gould, S. A., Rosen, A. L., Sehgal, L. R., Moss, G. S.: Red Cell Substitutes: Hemoglobin Solution or Fluorocarbon?, *J. Trauma*, 22:736, 1982; Gould, S. A., Rosen, A. L., Sehgal, L. R., Moss, G. S.: Hemoglobin Solutions as Red Cell Substitutes; *Trans. Am. Soc. Art. Int. Organs*, 26:350, 1980. Pyridoxylation followed by polymerization of stromo-free hemoglobin solutions has reduced many of the above problems except for high oxygen affinity and possibly toxicity. Also, the process generates some methemoglobin, which is a form of hemoglobin which cannot transfer oxygen. Sehgal, L. R., Rosen, A. L., Gould, S. A., Moss, G. S.: Polymerized Pyridoxylated Hemoglobin: A Red Cell Substitute with Normal Oxygen Capacity, Surgery, 95:433, 1984: Keipert, P. E., Chang, T. M. S.: Preparation and In-vitro Characteristics of Pyridoxylated Polyhemoglobin as Blood Substitutes, *Appl. Biochem. Biotechnol.* 10:133, 1984.

Encapsulation of hemoglobin solution in a synthetic cell has been attempted by encapsulating hemoglobin solution within nylon membranes, cross-linked protein membranes, polyhemoglobin membranes and liposomes encapsulating hemoglobin in phospholipid vesicles. Miller, I., Synthetic Blood Substitutes: Where Are We and Where Do We Go From Here?, CRC, *Crit. Rev. BioEng.*, 149–178, December 1978. Hemoglobin solution droplet encapsulation in a polymerized hemoglobin encapsulating membrane using glutaraldehyde as a crosslinking agent is described in "Artificial Red Cells with Crosslinked Hemoglobin Membranes", Thomas A. Davis, William J. Asher and Herbert W. Wallace, Applied Biochemistry and Biotechnology, Vol. 10, pgs. 123–132 (1984). The liposome encapsulated hemoglobin, although overcoming many of the problems encountered with other blood substitute products, are still too rapidly cleared from the circulatory system, are limited in oxygen carrying capacity, and have low encapsulation efficiencies, in the order of 10 to 20 percent. A method of scaled-up production of liposome-encapsulated hemoglobin described in U.S. Pat. No. 4,776,991 overcomes some of the problems pointed out above.

Preparation of multiple emulsions of water in oil in water using non-ionic emulsifiers, deionized distilled water and liquid paraffin with mixing to form the water in oil emulsion and homogenizing to form the oil in water emulsion is taught by "An Attempt at Preparing Water-in-Oil-in-Water Multiple Phase Emulsions", Sachio Matsumoto, Yashiko Kita and Daizo Yonezawa, Journal of Colloid and Interface Science, Vol. 57, No. 2, pgs. 353–361 (1976). Water in olive oil in water emulsions were prepared using a mixed soy lecithin and Span 80 emulsifier which interact to form a viscoelastic film at the oil/water interface and sucrose-fatty acid ester at the outer water phase is taught by "Preparation of Water-in-Olive Oil Multiple-Phase Emulsions in an Eatable Form", Sachio Matsumoto, Yoshiro Ueda, Yoshiko Kito, and Daizo Yonezawa, *Agric. Biol. Chem.*, 42, No. 4, pgs. 739–743 (1978).

SUMMARY OF THE INVENTION

This invention relates to a double liquid emulsion of an aqueous solution of an oxygen carrying material, such as hemoglobin, in oil in aqueous outer phase. The double liquid emulsion of this invention has a primary emulsifying agent to aid in the formation and maintenance of the primary emulsion of aqueous hemoglobin solution in oil. A secondary emulsifier is used in the formation and maintenance of the secondary emulsion of the primary emulsion in an aqueous outer phase. Thus, the primary emulsion may be made up of primary emulsion droplets each comprising individual droplets or a plurality of individual droplets of aqueous hemoglobin solution in the oil phase and the secondary emulsion is made up of secondary emulsion droplets each comprising individual droplets or a plurality of individual droplets of the primary emulsion suspended in the aqueous outer phase as shown schematically in FIG. 1.

The oil phase may comprise mineral or fixed oils which provide satisfactory emulsion stability. Suitable fixed oils include vegetable and animal oils. Suitable vegetable oils include; olive, safflower, sesame and soybean and suitable animal oils include those containing glycerol esters. By the term fixed oils we also mean to include triglycerides, regardless of source. Preferred mineral oils include: No. 40 white oil, Carnation light oil and Klearol light oil. Mixtures of these oils may be used.

In order to prepare the multiple emulsion of this invention, it is necessary to first prepare the primary emulsion and then in a separate process prepare the secondary emulsion. We have found that in preparing the primary emulsion it is necessary to first mix the components using a stirrer, such as a magnetic stirrer, followed by high shear mixing and cavitation through a microfluidizer. The secondary emulsion is separately prepared by either stirring alone, such as by magnetic stirring, or by stirring followed by low shear mixing, such as by a homogenizer, with the desired small size selection being achieved by filtration.

The multiple emulsions according to this invention, have the following properties:

|  | Broadest Suitable | Preferred |
| --- | --- | --- |
| Viscosity | 3–9 cp | 3–5 cp |
| Primary emulsion droplet size | up to 5 microns | up to 3 microns |
| Secondary emulsion droplet size after filtration | up to 10 microns | up to 8 microns |
| Yield | 85–99% | 95–99% |
| oxygen carrying capacity | 7–20 vol. % | 10–20 vol. % |

The sizes of the primary emulsion and secondary emulsion droplets are preferably as small as consistent with good stability: over 50 percent of freshly prepared primary emulsion droplets being smaller than 0.5 micron and over 50 percent of freshly prepared secondary emulsion droplets being smaller than 4 microns. The emulsions used in this invention may be macro-emulsions or micro-emulsions.

BRIEF DESCRIPTION OF THE DRAWINGS

The above objects and advantages of this invention will become more clear upon reading preferred embodiments of the invention and reference to the drawings wherein.

DESCRIPTION OF PREFERRED EMBODIMENTS

Figure 1:
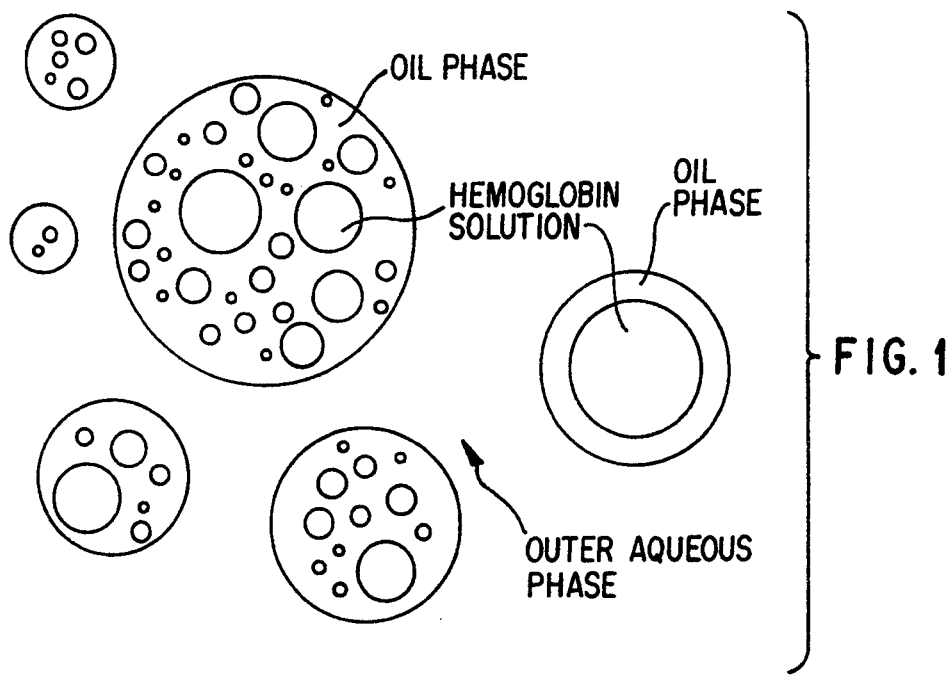
FIG. 1 is a schematic showing of an aqueous hemoglobin in oil in outer aqueous phase liquid double emulsion according to this invention.

An aqueous solution of any oxygen carrying material may be used in the primary emulsion portion of the multiple emulsion of this invention. Oxygen providing materials such as hemoglobin obtained from human blood or from bovine sources or modified hemoglobin such as pyridoxylated polyhemoglobin is suitable. The entire process is preferably carried out under refrigerated conditions of about 4° C. to about 8° C. to reduce formation of oxygen inactive methemoglobin. The process should also be carried out under aseptic conditions when the multiple emulsion is to be used as a blood substitute. All solutions used in preparing the multiple emulsion are filtered through a sterilizing filter during preparation of multiple emulsion for use as a blood substitute as well as the addition of antibiotics. The hemoglobin may be isolated from red blood cells by any suitable means known to the art and prepared in a relatively stroma-free aqueous hemoglobin solution concentrated from about 1 g % to about 35 g % and preferably from about 5 g % to about 35 g % hemoglobin. The aqueous hemoglobin solution, when used as a blood substitute may be dialyzed with phosphate buffered saline and may have added antibiotics, albumin, glucose, pyridoxol-5-phosphate (Vitamin A), and carbonic anhydrase.

Mineral or fixed oils are suitably used to formulate the primary emulsion. Preferred mineral oils are No. 40 white oil, viscosity 4–5 cst @ 40° C. SG 0.804–0.820 @ 25° C., maximum pour point 2° C., and minimum flash point 135° C.; Carnation light mineral oil, viscosity 11–14 cst at 40° C., SG 0.837–0.953 at 25° C. pour point −7° C., and minimum flash point at 177° C., and Klearol light mineral oil, viscosity 7–10 cst at 40° C., SG 0.822–0.833, pour point −7° C., and minimum flash point at 138° C.; (Witco Chemical Corp.) Preferred fixed oils include vegetable oils of sesame, olive, soybean and safflower vegetable oils (Croda Inc., Edison, N.J.) and oils comprising triglycerides, such as tricaproin, tricaprylin and tripalmitin. A primary emulsion emulsifier of the hydrophobic type having a lower HLB Number, such as polyoxypropylene-polyoxyethylene block copolymers (Pluronic L101, BASF Corp., Parsippany, N.J.), glycerol monooleate (Atmos 300, Kraft, Inc., Memphis, Tenn.), glycerol dioleate, sorbitan sesquioleate, polyoxyethylene alcohol, and sorbitan monooleate (Arlacel 186, Arlacel C, Brij 93, and Span 80, respectively, ICI Armerica, Inc., Wilmington, Del.) is dissolved in the oil phase in an amount of 2 to 30 volume percent and preferably 5 to 15 volume percent, based upon the total primary emulsion.

For a primary emulsion using mineral oil, the aqueous hemoglobin solution in an amount of about 40 to about 90 volume percent, preferably about 60 to about 70 volume percent; mineral oil in an amount of about 8 to about 58 volume percent, preferably about 14 to about 25 volume percent; and primary emulsifying agent in an amount of about 2 to about 30 volume percent, preferably about 5 to about 15 volume percent are mixed. For a primary emulsion using fixed oil, the aqueous hemoglobin solution in an amount of about 40 to about 90 volume percent, preferably about 40 to about 60 volume percent; fixed oil in an amount of about 5 to about 30 volume percent, preferably about 20 to about 30 volume percent; and primary emulsifying agent in an amount of about 5 to about 30 volume percent, preferably about 20 to about 30 volume percent are mixed. The aqueous hemoglobin solution is preferably slowly added to the rapidly stirring oil phase and mixed, such as by use of a magnetic stirrer, for about 15 minutes to about 60 minutes and preferably about 25 minutes to about 35 minutes. The mixed primary emulsion is then subjected to high shear emulsification providing shear rates of about 100,000 to about 5,000,000 and preferably about 500,000 to about 1,000,000 $s^{-1}$ such as by using a microfluidizer at a pressure drop of about 1000 to about 10,000 psi, preferably about 1000 to about 3000 psi, and most preferably about 1800 to about 2000 psi. More complete information regarding the microfluidizer is set forth in U.S. Pat. No. 4,533,254. The microfluidizer provides high sheer rates of short duration, a fraction of a second, without denaturation of proteins, such as hemoglobin. The primary emulsion is filtered, such as by using a 5 micron hydrophilic polyvinylidene difluoride filter (Duropore, Millipore Corp.). Albumin may be added to the hemoglobin solution prior to emulsification in amounts of about 1 to about 5 g %, preferably about 2 to about 3 g % to aid in stabilizing the multiple emulsion size distribution.

The primary emulsion of aqueous hemoglobin in mineral or fixed oil to be suitable for preparation of the liquid multiple emulsion of this invention, should result in primary emulsion droplet diameters in the range of less than 5, and preferably less than 3, microns.

The outer aqueous phase of the multiple emulsion may be any aqueous liquid dependent upon the use to which the multiple emulsion is placed. To serve as a blood substitute, the outer aqueous phase is preferably isotonic phosphate buffered saline of a pH of about 7.4. A secondary emulsion emulsifier having hydrophilic properties and a higher HLB Number is suitable, such as polyoxyethylene fatty acid esters, such as Tween 20, Tween 40, Tween 60, Tween 80 (ICI America Inc.) or an ethylene oxide, such as Pluronic F68 (BASF Wyandotte Corp.), preferably Tween 60 or Pluronic F68, is dissolved in the outer aqueous phase in an amount of 0.25 to 2 weight percent and preferably 0.25 to 0.75 weight percent, based upon the total outer aqueous phase. Egg lecithin, in the above amounts, has been found to be a satisfactory secondary emulsifier and may be a preferred secondary emulsifier for blood substitutes for administration to humans. Any desired water soluble additives may be added to the outer aqueous phase, such as albumin in amounts of 0.5 to 10 g % and dextran 0.5 to 5.0 g % which have been found to narrow size distribution and stabilize the multiple emulsion, and any other desired antibiotics like as mentioned above for hemoglobin solution.

In one embodiment, the primary emulsion, secondary emulsifying agent, and outer aqueous phase are mixed to form the secondary emulsion by dispersion, such as by a magnetic stirrer, for about 15 minutes to about 60 minutes, preferably about 25 minutes to about 35 minutes, to provide a uniform dispersion. It is preferred to first add the secondary emulsifier to the outer aqueous phase with mixing and then to add the primary emulsion to the outer phase in order to form the secondary emulsion. In another embodiment, which appears to provide enhanced long term stability, the secondary emulsion as mixed above is subjected to low shear mixing, such as by using a microfluidizer homogenizer at a pressure drop of about 200 to about 500 psi. More complete description and results of various combinations of emulsion mixing techniques are set forth in Zheng, S., Beissinger, R. L., and Wasan, D. T., The Stabilization of Hemoglobin Multiple Emulsion for Use as a Red Blood Cell Substitute, Journal of Colloid and Interface Science, Vol. 144, No. 1, pgs. 72–85, (June 1991) which is incorporated herein in its entirety by reference.

The final multiple emulsion suitably is in the proportion of about 10 to about 90, preferably about 35 to about 50 volume percent, of primary emulsion to about 10 to about 90, preferably about 50 to about 65, volume percent of outer aqueous phase of the secondary emulsion. The secondary emulsion may be filtered by any known technique to a final secondary emulsion product having desired secondary emulsion droplet sizes, both maximum and average size droplets. The droplets of the secondary emulsion prior to such filtration are about 20 to about 50 microns maximum size and about 10 to about 20 microns diameter average size and by filtering may readily be reduced to maximum droplet sizes of below 10 microns and average droplets of below 5 microns by passing up to three times through a filter such a 5 micron hydrophilic polyvinyledene difluoride filter resulting in a multiple emulsion suitable as a blood substitute.

The multiple emulsions produced in accordance with the process of this invention have been found to be very stable. The term "yield" as used herein expresses the amount of hemoglobin originally in the primary emulsion compared to the amount of hemoglobin leaked to the outer aqueous phase. More detailed information concerning encapsulation efficiency expressed as yield is found in Borwanker, C. N., S. B. Pfeiffer, Zheng, S, Beissinger, R. L., Wasan, D. T., Sehgal, L. R., and Rosen, A. L., Formulation and Characterization of a Multiple Emulsion for Use as a Red Blood Cell Substitute, Biotechnology Progress, Vol. 4, No. 4, 210–217, December 1988, incorporated herein in its entirety by reference. Following preparation, the yield of the multiple emulsions has been found to be about 99 percent prior to filtering and after three filter passes through a 5 micron filter reduced to above 97 percent. White oil and triglyceride oil based multiple emulsions have been found to result in highest yield (above 98 percent), vegetable oils safflower, soybean, sesame and olive have been found to result in multiple emulsions having yields above 81 percent, and mink oil gave the lowest yield of oils tested at about 62 percent. The yield decreases during storage, but has been found to be above 85 percent following 23 days of storage under refrigerated conditions. Droplet sizes of the multiple emulsion increase with storage at refrigerated temperatures, for example, from a fresh average size of 3.8 microns to about 10 microns at 16 days and 15 microns at 23 days. Size distribution similar to the freshly prepared double emulsion can be obtained by one to three filtrations through a 5 micron filter as used in the original preparation. Oxygen carrying capacity of the multiple emulsion provides an oxygen content of about 14 ml $O_2$ per 100 ml of multiple emulsion and decreases to about 10 after 23 days of storage.

While the multiple emulsions of this invention may be used for various oxygen provision systems, an important aspect of this invention is the suitability of the multiple emulsions for use as a blood substitute. The droplet sizes of the multiple emulsion are suitable for use in a cardiovascular system. The steady shear viscosity of the multiple emulsion over the shear rate range expected in the cardiovascular system is about the same as that of whole blood and exposing the multiple emulsion to the shear rate range noted results in negligible change in yield, that is, negligible release of hemoglobin solution to the outer phase of the multiple emulsion. The oxygen carrying capacity of the multiple emulsion of this invention is similar to that of blood. We have found that differences in colloid osmotic pressure between the inner hemoglobin phase and the outer aqueous phase (109 mm Hg and 25 mm Hg, respectively) does not cause significant effect upon leakage of hemoglobin from the inner emulsion and has little effect upon size distribution of the multiple emulsion droplet, even after 3 days storage. From these properties and the physiological compatibility of an outer phosphate buffered saline aqueous phase, it would be expected that the multiple emulsions would be suitable for use as blood substitutes. As shown in the specific examples, multiple emulsions prepared according to this invention do not show acute toxicity when injected into mice as blood substitutes and can support life in rats whose hematocrit has been reduced to levels which are otherwise incompatible with survival. The hemoglobin multiple emulsions of this invention may also be useful in the oxygenated preservation of donated body organs, as the oxygen exchange fluid in blood oxygenators, and the oxygen supplier in mammalian cell cultures.

The following specific Examples are set forth in detail to afford a better understanding of the invention, but should not be considered as limiting the invention.

EXAMPLE I

Figure 2:
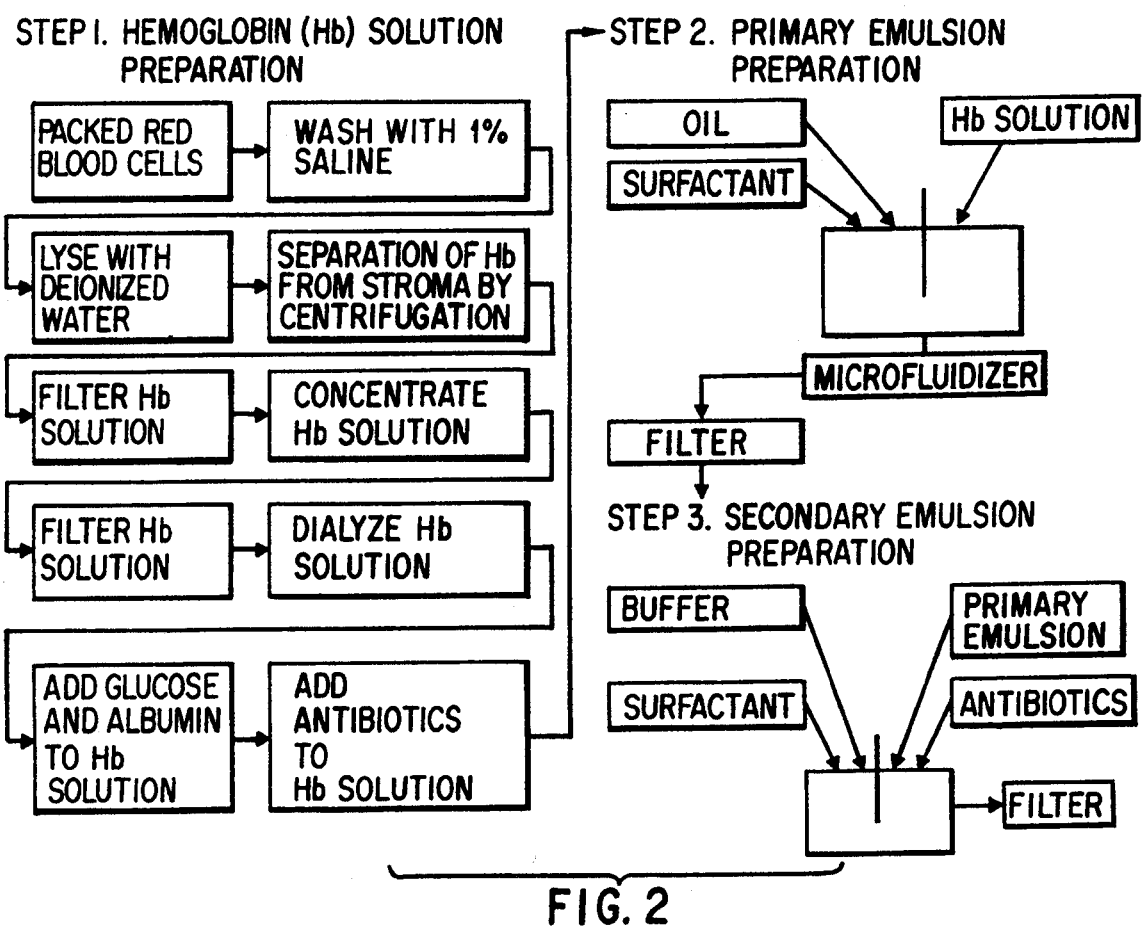
FIG. 2 is a simplified diagram of the steps of a process according to this invention.

A hemoglobin double emulsion was prepared by first preparing a hemoglobin in No. 40 white mineral oil primary emulsion followed by preparing a secondary emulsion of the primary emulsion in an aqueous phosphate buffered saline solution. FIG. 2 outlines the process followed in this Example.

A hemoglobin saline solution was prepared by washing red blood cells with 1.0 weight percent sodium chloride in deionized water at a volume ratio of 1:1 by gently mixing followed by centrifugation at 4000×g for ten minutes in a refrigerated centrifuge. After centrifugation, the buffy coat and supernatant were discarded and the washing procedure repeated until the supernatant was clear, usually 1 to 3 times. After washing, the packed red blood cells were lysed by dilution with 4 to 5 volumes of deionized water and the resulting mixture agitated for 12 hours using a magnetic stirrer in a refrigerator. The stroma, mainly red blood cell membrane fragments, were removed by centrifugation at 30,000×g for 30 minutes. The supernatant hemoglobin solution was removed and concentrated in a Minitan (Millipore Corp., Bedford, Mass.) cross flow ultrafiltration system using eight polysulfone 30,000 nominal molecular weight filter packets, the solution maintained in an ice bath during the entire concentration process to reduce the formation of methemoglobin. The concentration procedure was continued until the cross filtration flow rate had to be drastically reduced in order not to exceed the maximum recommended back pressure of the ultrafiltration system. The hemoglobin solution following concentration was up to 35 g %, 35 grams hemoglobin per 100 ml solution. The hemoglobin concentrate was dialyzed against 30 mM phosphate buffered saline to provide desired osmotic equilibrium with the outer aqueous phase. The pH of the phosphate buffer was adjusted as necessary, from 7.4 to 8.0, to assure that the pH of the dialyzed hemoglobin solution was about 7.4. The dialyzed hemoglobin solution was centrifuged at 30,000×g for 30 minutes and then filtered using 0.20 micron sterilizing filters (Fisher Chem. Co.) to remove any stroma material that precipitated due to the pH adjustment. Antibiotics were added to the hemoglobin solution to provide on a liter basis, penicillin—5000 units, Gentamicin—40 mg, Polymyxin—2500 units, and Streptomycin—50 mg. Also, the addition of human albumin and glucose resulted in 2.5 g % and 3.5 g % solutions, respectively.

The primary hemoglobin in oil emulsion was prepared using a magnetic stirring table by slowly adding the above prepared hemoglobin solution to a vigorously stirred white mineral oil No. 40 (Witco Chemical Corp.) containing 15 weight percent polyoxyethylene alcohol surfactant Brij 93 (ICI Americas Inc.). Slow addition of the hemoglobin solution to the vigorously stirred oil phase achieved high loading of the aqueous phase, 60 volume percent loading of hemoglobin solution in the oil phase. The hemoglobin-oil mixture was subjected to high energy emulsification under refrigerated conditions using an M 110 Microfluidizer Model BO4 with D-20 inserts (Microfluidics Corp.) at a pressure drop of 2000 psi with shear of about $1 \times 10^6 s^{-1}$ to achieve small multiple emulsion droplets and to increase the stability of the primary emulsion. The primary emulsion was then filtered using a 5 micron hydrophilic polyvinylidene difluoride filter (Durapore, Millipore Corp.).

The outer aqueous phase of the multiple emulsion was isotonic phosphate buffered saline of pH 7.4, selected for its physiological compatibility, to which was added 0.5 g % surfactant polyoxyethylene fatty acid esters Tween 60 (ICI America Inc.), 1 g % albumin and 0.5 g % dextran (62,400 MW, Sigma Chemical Company).

The above prepared primary hemoglobin in oil emulsion was then dispersed in the above prepared outer aqueous phase at a 1:1 volume ratio by mixing for 30 minutes with a magnetic stirrer. The multiple emulsion was filtered 3 times to reduce the maximum droplet size to below 10 microns and the average size of the droplets to below five microns by filtering through a 5 micron hydrophilic polyvinylidene difluoride filter (Durapore, Millipore Corp.) into a collection flask. The filtration was carried out under a slight vacuum of 25 kPa obtained by water aspiration which provided a filtration rate of about 5 ml per minute. When the multiple emulsion was prepared in a manner suitable for blood substitutes, all solutions used in the preparation of the multiple emulsion were sterilized by passage through a 0.2 micron filter.

Variation of pressure drop of the microfluidizer between 1000 and 3000 psia in preparation of the primary emulsion resulted in yields greater than 85 percent, peaking at 1800–2000 psia at 98 percent.

EXAMPLE II

A hemoglobin double emulsion was prepared as in Example I except that sesame vegetable oil was used in the primary emulsion. The aqueous hemoglobin solution containing 35 g % hemoglobin, and 3 g % human albumin was slowly (1 ml/min) added to the rapidly stirred oil phase which contained 50 weight percent Span 80, on basis oil phase, at a volume ratio of 40 volume percent, hemoglobin solution to 60 volume percent sesame oil for about 40 minutes and then subjected to high energy emulsification as described in Example I. The primary emulsion of aqueous hemoglobin in sesame oil was then dispersed in the outer aqueous phase of isotonic phosphate buffered saline which contained 1.0 weight percent human albumin, 0.5 weight percent dextran and 0.5 weight percent Pluronic F68 at a 1:1 volume ratio by mixing with low speed stirring for about 5 minutes. The multiple emulsion was filtered three times through a 5 micron filter to reduce the maximum droplet size to below 10 and average droplet size to below 4.

EXAMPLE III

Samples of freshly prepared multiple emulsion prepared as described in Example I were diluted with outer aqueous phase and placed in a Howard Cell (Rascher & Betzold Inc., Chicago, Ill.) and photographed through a MicrOmaster Phase Contrast Microscope (Fisher Scientific Inc.) using an Olympus OM1 camera. Droplet sizes were measured from the negatives with an MOP-3 semi-automatic image analyzer (Carl Zeiss Inc.) The primary emulsion maximum droplet diameters were less than 1.5 microns with an average size of less than 0.5 micron. Following 5 days storage at 4° C. the maximum and average primary emulsion droplet diameters were 2.5 and 0.5, respectively. The size distribution of the primary emulsion droplets were found to be narrowed and stabilized with time by the addition of the albumin.

The maximum and average multiple emulsion droplet sizes were about 7 and 3.8 microns, respectively, for fresh emulsions; 10 and 4.8 microns, respectively, for 4 day old emulsions; 15 and 10 microns, respectively, for 15 day old emulsions; and 20 and 15 microns, respectively, for 23 day old emulsions, all maintained at 5° C. The albumin added to the outer aqueous phase resulted in decreased droplet size and significantly decreased droplet growth during storage. It was also found that the number of filter passes using the 5 micron filter was important. A second filter pass resulted in reducing the maximum size from about 35 to about 15 microns and a third pass reduced the maximum size to about 7 microns.

EXAMPLE IV

The yield, expressed by the amount of hemoglobin encapsulated in the primary emulsion compared to the amount leaked to the outer phase, was measured using the multiple emulsion prepared in Example I. The number of filter passes using the 5 micron filter reduced the yield from just below 99 percent prior to filtering to above 97 percent after three filter passes. The yield of the multiple emulsion during storage decreases, but after 7 days of storage at 5° C. was measured to be above 91 percent and after 23 days of storage at 5° C. was measured to be above 85 percent.

EXAMPLE V

The bulk viscosity of the multiple emulsion prepared in Example I was measured with a Wells-Brookfield Syncro-Lectric Microviscometer, Model LVT equipped with a 0.8° cone Model CP-40 (Brookfield Engineering Laboratories, Inc., Stoughton, Mass.) and with a Weissenberg Rheogoniometer Model R16/R19 equipped with a 10 cm 0.3° cone and plate, platen system. The steady shear viscosity of the multiple emulsion varied from about 5 cp at a shear rate of 50 $s^{-1}$ to 3.5 cp at a shear rate of 500 $s^{-1}$. This approximates the shear rate of whole blood in a cardiovascular system. Under such shear rates, the yield remained about constant and the shear rate had little effect on size distribution of the multiple emulsion droplets between shear rates of 45 $s^{-1}$ and 450 $s^{-1}$.

The steady shear viscosity of the multiple emulsion prepared in Example II was 3 cp.

EXAMPLE VI

The oxygen carrying capacity, that is the oxygen content, of the multiple emulsion prepared in Example I was measured using a modification of Neville's biotonometry method (Neville, J. R. *J.Applied Physiology*, 37: 967, 1974) in a Warberg manometer (Fisher Scientific, Itasca, Ill.). Freshly prepared emulsion was measured to be about 14 ml $O_2$/100 ml multiple emulsion sample falling to about 10 ml $O_2$/100 ml multiple emulsion following 23 days of storage at 5° C.

The freshly prepared emulsion of Example II had an oxygen content of 10 ml $O_2$/100ml multiple emulsion.

EXAMPLE VII

Figure 3:
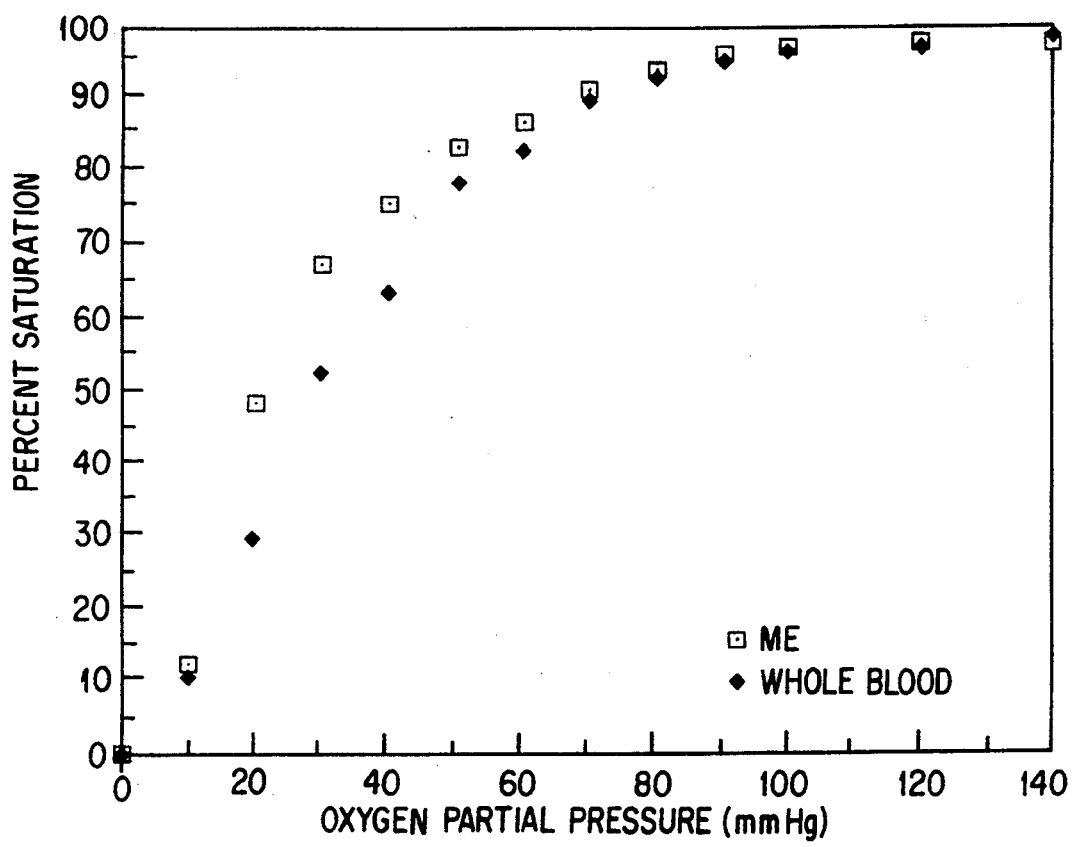
FIG. 3 is a graph showing the oxygen dissociation of a hemoglobin in oil in outer aqueous phase liquid multiple emulsion (ME) of this invention compared to whole blood.

A multiple emulsion was prepared in the manner described in Example I for use as a blood substitute except that the primary emulsion also contained pyridoxal-5-phosphate P-5-P (Sigma Chemical Company) at a molar ratio twice that of hemoglobin. P-5-P reduced the oxygen affinity to a $P_{50}$ value of 20 mm Hg compared to a measured $P_{50}$ value of 26 mm Hg for whole blood. The measurements were made at pH 7.35, $P_{CO}$ of O mm Hg, and temperature of 37° C. The oxyhemoglobin dissociation curve was measured using the modified biotonometry method and the results shown in FIG. 3 suggest a cooperativity similar to that of whole blood.

EXAMPLE VIII

A multiple emulsion was prepared in the manner described in Example I except that the primary emulsion contained 32.8 g % hemoglobin solution and the primary emulsion contained Carnation white mineral oil and made up 30 volume percent of the multiple emulsion. 0.55 ccs of this multiple emulsion was injected into four mice. All the animals survived and continued to exhibit a healthy appearance for up to several days after the injections.

Another multiple emulsion was similarly made up containing 35 volume percent primary emulsion and 1.0 cc was administered to three mice, all of which survived and appeared healthy for up to several days following injection.

A multiple emulsion was made up as described immediately above wherein the primary emulsion made up 50 volume percent of the multiple emulsion. This emulsion was injected with a 0.5 cc amount into five mice. All the animals survived and continued to appear healthy for up to several days after the injections.

All the above tests indicate no acute toxicity of the hemoglobin multiple emulsion using mineral oil occurred in these mice.

EXAMPLE IX

A multiple emulsion was prepared in a manner described in Example VIII except that sesame vegetable oil as described in Example II was used instead of mineral oil. The primary emulsion contained 35 g % hemoglobin solution. The multiple emulsion contained 50 percent primary emulsion and 50 percent outer aqueous phase. 0.5 and 1.0 cc of this multiple emulsion was injected into two mice, both of which survived and continued to appear healthy for several days.

The above tests indicate no acute toxicity of the hemoglobin multiple emulsion using sesame oil occurred in these mice.

EXAMPLE X

Figure 4:
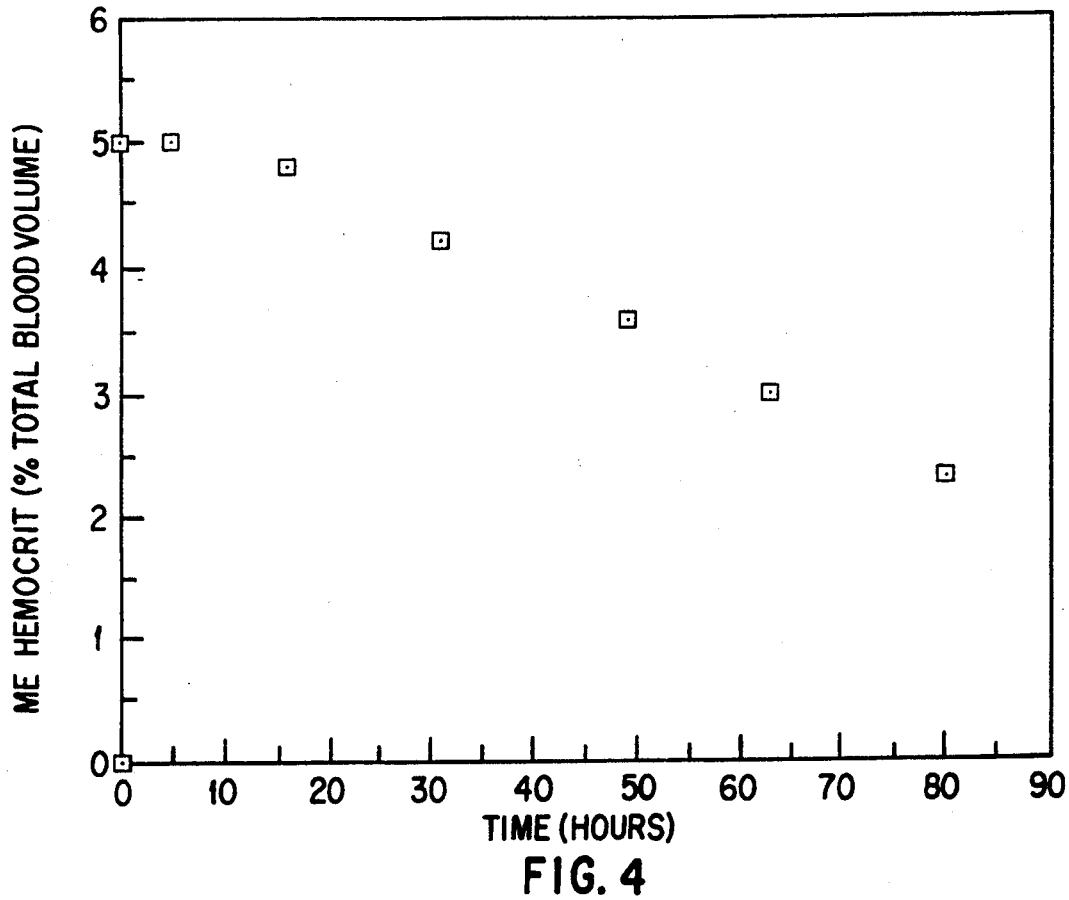
FIG. 4 is a graph showing the half-life of a hemoglobin in oil in outer aqueous phase liquid double emulsion of this invention in mice.

A multiple emulsion was prepared in a manner described in Example VIII with 35 volume percent primary emulsion for use as a blood substitute and was injected into five mice. Immediately following the injection step, a blood sample was collected in a microhematocrit tube. The multiple emulsion measured, after a 10 minute centrifugation, 5 volume percent of the animal's total blood volume. As shown in FIG. 4, the multiple emulsion dropped to 2 volume percent of the animal's total blood volume after 80 hours of circulation in the mice. Circulation half-life of the multiple emulsion in mice was determined to be about 70 hours.

EXAMPLE XI

A multiple emulsion was prepared in a manner described in Example VIII with 50 volume percent primary emulsion for use as a blood substitute. When mixed with platelet-rich plasma, no decrease in single platelets was observed.

EXAMPLE XII

A hemoglobin multiple emulsion was prepared in the following manner. The inner aqueous hemoglobin phase was prepared by washing red blood cells in plasma with 1 volume of 0.9% NaCl and cetrifuged at 4000×g for 10 minutes at 4° C. After centifugation, the buffy coat and supernatant was discarded. The wash was repeated as needed, normally 3 or fewer times, until the supernatant became clear. After washing, the red blood cells were lysed by dilution with four to five volumes of hypotonic buffer, and cell fragments were removed by centifugation at 30,000×g for 30 minutes at 4° C. The supernatant was removed, placed in an ultrafiltration system (Amicon CH-2, Danver, Mass.), and residual stroma removed using an Amicon 100,000 MW spiral cartridge. At this point, the concentration of the hemoglobin solution was approximately 2% and the solution was concentrated to 35 g % using an Amicon 30,000 MW spiral cartridge. The concentrated hemoglobin solution (pH approx. 6.6) was dialyzed against 30 mM phosphate buffered saline to achieve osmotic equilibrium with the outer aqueous phase to be used. The pH of the dialyzed hemoglobin solution was adjusted to 7.4 with 0.1N Trizma base and recentrifuged at 30,000×g for 30 minutes to remove any stroma which precipitated during the pH adjustment. To maintain the oxygen affinity of the multiple emulsion similar to that of red blood cells, pyridoxal-5-phosphate (P5P, Sigma Chemical Co., St. Louis, Mo.) was added to the hemoglobin solution at a molar ratio of 2:1 (P5P:Hb). Because the level of carbonic anhydrase in the hemoglobin solution may be reduced by the lysis and dialysis, carbonic anhydrase (Sigma Chemical Co.) was added to result in a concentration of about 2.5 mg/ml., similar to fresh red blood cells. To inhibit bacterial growth, 50,000 units of penicillin, 25,000 units of polymixin, 50 mg of streptomycin, and 40 mg of gentamycin were added per liter of hemoglobin solution. An antioxidant free radical scavenger catalase in the amount of 0.01 g per gram of hemoglobin was added to the hemoglobin solution.

The oil phase was prepared by heating to about 50°–60° C. alpha-tocopherol in an amount of about 1 mol %, 1 g % egg lecithin (American Lecethin Co., Atlanta, Ga.), and cholesterol (Sigma) in an amount of 1 mol per mol of egg lecithin were dissolved in purified white oil (Carnation oil, Witco Chemical Co., New York, N.Y.) containing primary emulsifier of 25 g % Span 80 (ICI America, Inc.).

The aqueous hemoglobin/oil primary emulsion was prepared by adding the hemoglobin solution slowly to the oil phase which was stirring vigorously on a magnetic stirring table. A 40 to 60 vol % loading of hemoglobin solution was used. The aqueous hemoglobin/oil emulsion formed by stirring was then subjected to high shear processing, to increase stability of the primary emulsion and to enable subsequent formation of smaller multiple emulsion droplets, using a M110 Microfluidizer or H-5000A Homogenizer (Microfluidics Corp, Newton, Mass.) at a pressure drop of 2,000 to 5,000 psig. The interaction chamber, reservoir and receiving vessel were refrigerated prior to use to avoid temperature increases which accompany high shear processing.

Isotonic 30 mM phosphate buffered saline was used as the outer aqueous phase. 0.3 g % Pluronic F68 (BSAF, Wyandotte Corp., Parsippany, Mich.) was added as a secondary emulsifier and colloidal material, primarily dextran (40,000 MW) was added to make the aqueous outer phase isotonic with respect to blood plasma and tissues by measurement of colloidal osmotic pressure with a Wescor Oncometer (Logan, Utah) The microfluidized aqueous hemoglobin/oil primary emulsion was then dispersed in the outer aqueous phase by mixing for 30 minutes by magnetic stirring to form the aqueous hemoglobin solution/oil/aqueous outer phase multiple emulsion. The multiple emulsion was then subjected to low shear treatment with a H-5000A Homogenizer at a pressure drop of about 200 psi across the interaction chamber. The homogenized double emulsion was filtered two or three times to reduce the maximum and average size of the multiple emulsion droplets to below 4 and 2 microns, respectively. Filtration was carried out at 4° C. under a light vacuum, 25 kPa, created by water aspiration through a 25 mm glass funnel, a fitted glass filter holder, 3 or 5 micron hydrophilic polyvinylidene difluoride filters (Durapore, Millipore Corp., Milford, Mass.) into a 125 ml collection flask. The filtration rate was about 10 ml per minute. After filtration, the multiple emulsion was stirred continuously at a slow rate and maintained at 4° C. for storage. The maximum size of the primary emulsion droplets was less than 1 micron and the maximum size of the multiple emulsion droplets was less than 8 microns with an average size of 2–3 microns.

The encapsulation efficiency of the multiple emulsion prepared by stirring was 95–98% with average droplet size of 3-4 microns and a maximum droplet size of 6-8 microns while the encapsulation efficiency of the multiple emulsion prepared by homogenization was 90-95% with average droplet size of 2-3 microns and a maximum droplet size of 4-6 microns. The multiple emulsion formulation using homogenization improved emulsion stability by decreasing droplet diameter while maintaining high hemoglobin encapsulation efficiency.

Storage of the multiple emulsion over a six day period showed encapsulation efficiency initially at 98 percent reduced to 92-94 percent and oxygen content reduced from an initial 13.8 volume percent to 13.3 volume percent. The maximum size of the multiple emulsion droplets increased over the six day period from 6-8 to about 20 microns and the average size incresed from 2-3 to 6 microns. However, when the stored samples were filtered twice through 5 micron filters without affecting the yield and oxygen content, the average and maximum droplet sixe were about the same as the fresh multiple emulsion.

Steady shear viscosity of the multiple emulsion for a volume fraction ratio of droplets to outer aqueous phase of 1:1 was from 4.6 to 3.2 centipoise for shear rates of about 500 $s^{-1}$ at 37° C. Values determined from the oxygen saturation curve .for the multiple emulsion for oxygen affinity was $P_{50}$ of 20 mm Hg and for cooperativity was Hill coefficient of 2.4, both comparing favorably with those of whole blood.

EXAMPLE XIII

Efficacy studies were performed using the multiple emulsion described in Example XII in exchange transfusions in 8-12 week old Sprague-Dawley rats in pairs, one control and one experimental. The control rats received a sterile solution of 5.2 wt % dextran (40,000 MW) in PBS to serve as a non-toxic volume expander without oxygen carrying capacity. In control rats exchanged with dextran solution, mortality was observed at a mean hematocrit of 5.1 0.8% and 100 percent mortality was observed at a hematocrit of 4.5% which corresponds to an exchange of about 90 percent. Rats exchanged with the aqueous hemoglobin/oil/water multiple emulsion survived to a mean hematocrit of 2.6 0.6% (range of 2.2 to 3.4%), an exchange of approximately 95 percent. This difference is significant at the 1% level. Although the number of animals tested was small, 30, these data provide a demonstration of the hemoglobin/oil/water multiple emulsion in maintaining survival at hematocrits below 4.5% where 100 percent mortality was observed in rats transfused with a plasma expander. Studies showed that blood pressure, heart rate and respiration rate were unaffected during 50% isovolemic exchange-transfusions of blood with the multiple emulsion.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

We claim:

1. An oxygen containing multiple liquid emulsion comprising a primary emulsion comprising aqueous solution of oxygen carrying material in oil selected from the group consisting of vegetable oil, animal oil triglyceride and mixtures thereof, emulsified with a primary emulsifier having primary emulsion droplet sizes of up to about 5 microns and a secondary emulsion comprising said primary emulsion in an outer aqueous phase emulsified with a secondary emulsifier having secondary emulsion droplet sizes up to about 10 microns, said multiple emulsion having a viscosity of about 3 to about 9 cp, yield about 85 to about 99 percent, and oxygen carrying capacity about 7 to about 20 volume percent.

2. An oxygen carrying multiple emulsion according to claim 1 wherein said oxygen carrying material is hemoglobin.

3. An oxygen carrying multiple emulsion according to claim 1 wherein said oil is triglyceride.

4. An oxygen carrying multiple emulsion according to claim 1 wherein said primary emulsion comprises about 40 to about 90 volume percent said aqueous solution of oxygen carrying material about 8 to about 58 volume percent said oil, and about 2 to about 30 volume percent said primary emulsifier.

5. An oxygen carrying multiple emulsion according to claim 1 wherein said primary emulsion comprises about 60 to about 70 volume percent said aqueous hemoglobin, about 14 to about 25 volume percent said oil, and about 5 to about 15 volume percent said primary emulsifier.

6. An oxygen carrying multiple emulsion according to claim 1 wherein said primary emulsion droplet sizes are up to about 3 microns and said secondary emulsion droplet sizes are up to about 8 microns.

7. An oxygen carrying multiple emulsion according to claim 1 wherein said oxygen carrying material is hemoglobin, said oil is triglyceride oil selected from the group consisting of tricaproin, tricaprylin, tripalmitin and mixtures thereof, said primary emulsifier is selected from the group consisting of Pluronic L101, Atmos 300, Arlacel 186, Arlacel C, Brij 93 and Span 80, said primary emulsion comprises about 40 to about 90 volume percent said aqueous hemoglobin, about 5 to about 30 volume percent said triglyceride oil, and about 5 to about 30 volume percent said primary emulsifier, said secondary emulsifier is selected from the group consisting of Tween 20, Tween 40, Tween 60, Tween 80, Pluronic F68, and egg lecithin, said multiple emulsion comprises about 10 to about 90 volume percent said primary emulsion, about 10 to about 90 volume percent said outer aqueous phase, and about 0.25 to about 2 weight percent said secondary emulsifier, said yield is about 85 to about 99 percent, and said oxygen carrying capacity is about 10 to about 20 volume percent.

8. An oxygen carrying multiple emulsion according to claim 1 wherein said aqueous solution of oxygen carrying material additionally comprises about 0.5 to about 5 g % albumin.

9. An oxygen carrying multiple emulsion according to claim 1 wherein said outer aqueous phase additionally comprises about 0.5 to about 10 g % albumin.

10. An oxygen carrying multiple emulsion according to claim 1 wherein said oxygen carrying material comprises hemoglobin solution of about 1 to about 35 gram percent hemoglobin.

11. An oxygen carrying multiple emulsion according to claim 1 wherein said outer aqueous phase additionally comprises about 0.5 to about 5 g % dextran.

12. An oxygen carrying multiple emulsion according to claim 1 wherein said primary emulsifier is selected from the group consisting of polyoxypropylene-polyoxyethylene block copolymers, glycerol monooleate, glycerol dioleate, sorbitan sesquioleate, Brij 93 polyoxyethylene alcohol, sorbitan monooleate and mixtures thereof and said secondary emulsifier is selected from the group consisting of polyoxyethylene fatty acid esters, Pluronic F68 ethylene oxide, egg lecithin and mixtures thereof.

13. An oxygen carrying multiple emulsion according to claim 1 wherein said oil is triglyceride selected from the group consisting of tricaproin, tricaprylin, tripalmitin and mixtures thereof.

14. An oxygen carrying multiple emulsion according to claim 1 wherein said primary emulsion comprises about 40 to about 90 volume percent said oil, based upon said primary emulsion, and said primary emulsion comprises about 10 to about 90 volume percent and said outer aqueous phase comprises about 10 to about 90 volume percent, based upon said multiple liquid emulsion.

15. A blood substitute comprising a sterile oxygen carrying multiple emulsion comprising a primary emulsion comprising aqueous solution of oxygen carrying material in oil selected from the group consisting of vegetable oil, animal oil triglyceride and mixtures thereof, emulsified with a hydrophobic primary emulsifier having primary emulsion droplet sizes of up to about 5 microns and a secondary emulsion comprising said primary emulsion in an outer aqueous phase emulsified with a hydrophilic secondary emulsifier having secondary emulsion droplet sizes up to about 10 microns, said multiple emulsion having a viscosity of about 3 to about 9 cp, yield about 85 to about 99 percent, and oxygen carrying capacity about 7 to about 20 volume percent.

16. A blood substitute according to claim 15 wherein said oxygen carrying material is hemoglobin.

17. A blood substitute according to claim 15 wherein said aqueous solution of oxygen carrying material additionally comprises about 0.5 to about 5 g % albumin.

18. A blood substitute multiple emulsion according to claim 15 wherein said outer aqueous phase additionally comprises about 0.5 to about 10 g % albumin.

19. A blood substitute according to claim 15 wherein said primary emulsion comprises about 40 to about 90 volume percent said oil, based upon said primary emulsion, and said primary emulsion comprises about 10 to about 90 volume percent and said outer aqueous phase comprises about 10 to about 90 volume percent, based upon said multiple liquid emulsion.

* * * * *